(12) United States Patent
John et al.

(10) Patent No.: US 6,271,410 B1
(45) Date of Patent: Aug. 7, 2001

(54) HIGHER ALKYL ESTERS OF CYANOACETIC ACID

(75) Inventors: Thomas V. John, Yardley, PA (US); Chitoor S. Subramaniam, East Brunswick; Mark Whipkey, North Plainfield, both of NJ (US)

(73) Assignee: Creanova Inc., Somerset, NJ (US)

( * ) Notice: Subject to any disclaimer, the term of this patent is extended or adjusted under 35 U.S.C. 154(b) by 0 days.

(21) Appl. No.: 09/589,561

(22) Filed: Jun. 6, 2000

(51) Int. Cl.$^7$ ................................................. C07C 255/00
(52) U.S. Cl. .............................................................. 558/443
(58) Field of Search ............................................... 558/443

(56) References Cited

U.S. PATENT DOCUMENTS 5,756,807 * 5/1998 Grund et al. ........................ 558/443

* cited by examiner

Primary Examiner—Joseph K. McKane
Assistant Examiner—Joseph Murray
(74) Attorney, Agent, or Firm—Abelman, Frayne & Schwab

(57) ABSTRACT

$C_{3-12}$ alkyl, substituted alkyl, alkenyl and cycloalkyl cyanoacetates are prepared by an efficient and simplified one-step process in which a small molar excess of the corresponding alcohol, i.e., $C_{3-12}$ alkyl, substituted alkyl, alkenyl or cycloalkenyl alcohol is reacted with crystalline cyanoacetic acid, or a concentrated aqueous solution of cyanoacetic acid, in the presence of an acid catalyst, such as, for example, methanesulfonic acid, p-toluenesulfonic acid, sulfuric acid and phosphoric acid at a temperature in the range of from about 60° C. to about 150° C., in accordance with the following reaction:

$$CNCH_2COOH + R\text{—}OH \xrightarrow{(cat)} CNCH_2COOR + H_2O \qquad (I)$$

where R is a $C_{3-12}$ alkyl, substituted alkyl, alkenyl or cycloalkyl.

17 Claims, No Drawings

HIGHER ALKYL ESTERS OF CYANOACETIC ACID

BACKGROUND OF THE INVENTION

1. Field of the Invention

The present invention relates to a process for production of cyanoacetates and, more specifically, to an esterification process for producing cyanoacetates by reacting crystalline cyanoacetic acid, or its concentrated pure 90% aqueous solutions, with a $C_{3-12}$ alkyl, substituted alkyl, alkenyl, or cycloalkyl alcohol.

2. Description of the Prior Art

Cyanoacetates are important intermediates in the manufacture of cyanoacrylates, agricultural chemicals, cosmetics, pharmaceuticals, and a variety of other commercial and industrial products. There has been a continuing interest in the preparation of cyanoacetates from higher alkyl esters of cyanoacetic acid. As used herein, "higher alkyl esters" shall mean $C_3$–$C_{12}$ compounds.

For example, Yonezawa et al., have reported on the manufacture of alkyl cyanoacetates by the esterification of cyanoacetic acid with alcohols in the presence of sulfuric acid as a catalyst in an article entitled "α-Cyanoacrylates III: Esterification of Cyanoacetic Acid and Monochloroacetic Acid", Yuki Gosei Kagaku Kyokai Shi 24 (7), 580-7 (1966). The addition of benzene was required to effect the azeotropic removal of water that is produced during the esterification reaction.

A procedure similar to that reported by Yonezawa et al. for the preparation of alkylcyanoacetates was later reported by Abdurakhimov et al. in "Cyanoacetate Esters", Tr. Tashk. Politek. Inst. (1973), 91 35–40 (Russian).

A process to make methyl and ethyl cyanoacetates was described by Mendow in "A Continuous Esterification of Substituted Acetic Acid with Aliphatic Alcohols," East German Patent DD 127117 770907 (1977). However, the process as disclosed is of little commercial interest since the recycling of unreacted alcohol is complicated by the presence of additional solvent that is involved in the process.

A modification of the foregoing process, namely, the use of a reactant as a solvent is disclosed in published German Patent Application 19617991.2 dated May 4, 1996. However, this approach is limited to alcohols with 3 carbon atoms or less, while the practical utilization of the process is further limited to methanol. As a further disincentive to the commercialization of this process is the requirement for specialized apparatus for conducting the reaction in a number of stages.

A process for esterification of cyanoacetic acid in an aqueous medium in disclosed in U.S. Pat. No. 5,347,032. The aqueous medium is comprised of an aqueous solution of cyanoacetic acid, which in a preferred embodiment is introduced as the crude stream directly from the acid synthesis. Although all of the examples are limited to butanol, it is disclosed that from 5 to 30 moles of a $C_4$ to $C_{10}$ alkanol are to be added per mole of acid in the aqueous medium. The process of the '032 patent thus requires a reaction vessel and related equipment capable of handling a large excess of water and alcohol, even before the reaction is commenced. In addition to the large-capacity equipment requirement, substantial utilities must be expended in heating and distilling off the water-alcohol azeotrope in order to drive the esterification reaction towards completion. The use of a crude acid synthesis stream will also produce undesirable impurities, such as esters of various mono- and dicarboxylic acids, as well as inorganic salts, in the reaction mixture with the cyanoacetate product.

A process for producing both butyl cyanoacetate and cyanoacetic acid is disclosed in U.S. Pat. No. 3,668,231 to Rosin et al. This patent discloses a process for the synthesis of cyanoacetamide in which an alkyl cyanoacetate is formed as an intermediate. Cyanoacetic acid is prepared as an aqueous solution without removing any of the inorganic salts produced. Water is present in such a relatively small amount that the concentration of salt in the reaction mixture is high so that the reaction mixture is virtually insoluble in a higher alkanol such as n-butanol, thereby permitting use of the higher alkanol to extract the cyanoacetic acid from the mixture. Following extraction of the cyanoacetic acid from the reaction mixture, the substantially water-free cyanoacetic acid reacts to esterify the alkanol in the presence of an esterification catalyst. During the course of the reaction, the water of esterification and lower alkanol are removed as an azeotrope. The process of the '231 patent is relatively complex from a commercial standpoint and not economically viable since it produces undesired by-products in relatively large quantities that must be disposed of by environmentally acceptable means.

It is therefore an important object of this invention to provide a one-step process for the commercial production of $C_3$–$C_{12}$ alkyl, substituted alkyl, alkenyl and cycloalkyl cyanoacetates in substantially quantitative yields based on the cyanoacetic acid starting material.

It is also an object of this invention to provide such an improved one-step process that is relatively economical to operate as compared to the processes of the prior art, both from the standpoint of equipment requirements and utilities consumed based on the amount of cyanacetate product produced.

It is yet another object of the invention to provide an improved reaction process with an efficient time-yield curve with little or no by-products that require processing for disposal.

SUMMARY OF THE INVENTION

It has now been found by us that $C_{3-12}$ alkyl, substituted alkyl, alkenyl and cycloalkyl cyanoacetates can be prepared by an improved and simplified one-step process in which a small molar excess of the corresponding alcohol, i.e., $C_{3-12}$ alkyl, substituted alkyl, alkenyl and cycloalkenyl alcohol, is reacted with cyanoacetic acid, or an aqueous solution of cyanoacetic acid, in the presence of an acid catalyst, such as, for example, methanesulfonic acid, p-toluenesulfonic acid, sulfuric acid and phosphoric acid at a temperature in the range of from about 60° C. to about 150° C., in accordance with the following reaction:

$$CNCH_2COOH + R\text{—}OH \xrightarrow{(cat.)} CNCH_2COOR + H_2O \qquad (I)$$

wherein R is a $C_{3-12}$ alkyl, substituted alkyl, alkenyl and cycloalkyl.

Although reaction scheme (I) indicates that equimolar quantities of acid and alkanol will react to produce the desired cyanoacetate product, it has surprisingly been found that the presence of a relatively small molar excess of the ROH alkanol (as compared to that taught by the prior art) has the effect of greatly improving the reaction equilibrium and results in the production of the desired cyanoacetate product in high yields of excellent purity.

Despite the residence time of from about 1 to about 5 hours of the thermally unstable cyanoacetic acid in the reaction zone, such time periods being needed to effect the removal of water, the yield of the esters is in the range of about 90% or greater, which is deemed a very high yield for esterification reactions. Moreover, the purity of the esters is typically about 98%, or even greater.

It is extremely significant that, in accordance with the practice of the process of the present invention, additional solvents are not needed to remove the water generated during the esterification reaction. This is in contrast to the prior art methods which teach the need for addition of such solvents. By the present process employing $C_3$–$C_{12}$ alcohols and other alkanols, generation of waste by-products can also be kept to a minimum by recycling the unreacted alcohol.

The improved process of the invention provides a simple one-step process that is especially suited for the commercial production of a large number of cyanoacetates. The process permits the use of commercial production equipment of relatively smaller capacity as compared to processes of the prior art for the same quantitative yields of cyanoacetate product. Most importantly, the process is more economical to operate than prior art processes employing larger molar excess of alcohol, water and added solvents, all of which require additional utilities to heat and eventually distill the fluids to remove them from the cyanoacetate product. The recycling or return of the alcohol distillate to the reaction vessel will provide a further savings in the costs of starting materials and utilities. The improved one-step process avoids the production of undesired and difficult to dispose of by-products.

DETAILED DESCRIPTION OF THE INVENTION

In accordance with the present invention, the alcohols used in the esterification reaction are preferably those from which water can be easily separated Representative alcohols which are suitable for this purpose include, but are not limited to, alkanols having from 3 to 12 carbon atoms, such as propanol, butanol, pentanol, isoamyl alcohol, hexanol, 2-ethyl hexanol, octanol and decyl alcohol.

While the esterification reaction of the present invention can be carried out in the absence of an esterification catalyst, the use of an acid catalyst to accelerate the rate of reaction is preferred in the commercial practice of the invention. Alkanesulfonic acids, such as methanesulfonic acid, are particularly preferred as the catalytic agent. Other suitable catalysts include alkylbenzenesulfonic acids, such as p-toluenesulfonic acid, and sulfuric acid and phosphoric acid. The quantity of catalyst employed is preferably in the range of from about 0.1 to about 1.0 percent by weight, based on the weight of cyanoacetic acid initially present in the reaction mixture.

Although an increase in temperature drives the reaction to a more rapid completion, the maximum temperature of the reaction should not exceed the boiling point of the ester being formed. The reaction is preferably carried out in the range of about 60° C. to 150° C., with from about 70° C. to about 120° C. being most preferred. The optimum temperature for carrying out the reaction depends upon the nature of the alkanol employed and the type of esterification catalyst being used. Lower temperatures are preferred when mineral acids, for example, sulfuric acid are employed and/or when low boiling alkanols such as propanol and butanol are used.

The stability of the particular cyanoacetate product must also be taken into consideration when selecting a temperature to drive the reaction. Of equal importance is the avoidance of unwanted by-products, which are generally formed at higher temperatures, and also the need to preserve the acid catalyst intact to allow the reaction to proceed to completion, or to a predetermined end-point. For example, when employing 2-ethylhexyl alcohol with methanesulfonic acid as a catalyst, the optimal esterification temperature was found to be between 70° to 130° C., with from about 100° C. to about 130° C. being most preferred.

In the practice of the process, cyanoacetic acid, an excess of the alcohol and an acid catalyst are introduced into a reaction vessel at ambient temperature or at a pre-selected temperature. Pre-selected temperatures and pre-heating of one or more of the reactants are useful to increase the solubility of the cyanoacetic acid in the mixture. The molar ratio of cyanoacetic acid to alcohol can be in the range of from 1:1.1 to 1:5, with a molar ratio of from about 1:1.1 to about 1:4 being preferred, and from about 1:1.2 to about 1:3 being most preferred. The addition to the reaction vessel of the cyanoacetic acid, the alcohol and the catalyst can be separately, or any two of the reactants can be premixed and added in combination, or all three can be added simultaneously.

As the reaction progresses and alcohol is carried from the reaction zone with the water being distilled off, additional alcohol is added in order to maintain the reaction mixture at the prescribed temperature, or within the prescribed temperature range. In one preferred embodiment, the alcohol is added from a fresh source of supply and is preferably preheated in order to maintain a stable temperature in the reaction zone. The replacement alcohol is preferably added as a continuous stream at a rate that is equivalent to that being removed as distillate with the water.

In another preferred embodiment of the process of the present invention, the alcohol that is removed by distillation from the reaction mixture with the water generated by the esterification reaction is returned to the reaction vessel after first separating the water from the mixture. It is important that any of the distillate alcohol that is returned to the reaction zone be dry, i.e., that it contain no, or substantially no water. In those instances where the alcohol and the water are not miscible, as is the case of alcohols such as 2-ethylhexyl, octyl, isoamyl, decyl and dodecyl alcohol, the upper layer of alcohol is continuously returned to the reaction vessel, while the lower layer which comprises water is discarded as a waste product.

The recycling or return of the alcohol distillate to the reaction vessel requires an additional step in those instances where the alcohol and the water form an azeotropic mixture. An azeotropic mixture of two or more liquids behaves like a single substance so that the vapor produced by the evaporation of the liquid has the same composition as the liquid even though the azeotropic mixture boils at a lower temperature than its individual constituents. Propanol, isopropanol and butanol form azeotropic mixtures and it is clearly advantageous to continuously process the alcohol-water azeotrope to expel the water therefrom in order to recycle or return the alcohol to the reaction vessel. This step can be accomplished by treating the water-alcohol azeotropic mixture with a suitable drying agent, such as, for example, phosphorus pentoxide, magnesium sulfate, or sodium sulfate. Alternatively, the azeotrope can be broken by extraction with a suitable extraction solvent such as, for example, toluene, xylene, pentane, hexane or cyclohexane, followed by distillation to remove the alcohol for recycling. The remaining water and solvent containing catalyst are discarded as waste. Processes and apparatus for practicing the separation step are well-known in the art.

The various components of the reaction mixture resulting from the esterification reaction are readily separated by fractional distillation by leaving the desired ester in high purity. The water and unreacted alcohol can be separated after distillation and the alcohol used either in the subsequent practice of the invention, or other processes.

A better understanding of the present invention can be obtained from the following examples, which are set forth for the purpose of illustration only, and are not to be construed as limiting the present invention in any respect. In each of the following examples the cyanoacetic acid is added in the form of technical grade dry crystals having a melting point of 66° C. In all examples, and in the preferred embodiment for the practice of the invention, an atmosphere of nitrogen is maintained in the reaction vessel.

EXAMPLE 1
Preparation of Ethylhexyl Cyanoacetate

Cyanoacetic acid (85.5 g; 1.0 mol), 2-ethylhexanol (172 g; 1.32 mol) and methanesulfonic acid (0.47 g; 0.005 mol) were introduced into a 500 ml flask under a nitrogen atmosphere. The reaction vessel was equipped with a distillation column that is provided with means for recycling the alkanol distillate to the flask. The mixture was heated slowly to a maximum of 130° C. while gradually reducing the pressure to about 15 mm of Hg. Water was continuously removed from the distillates (bp 68–80° C./100 mm Hg) and the organic layer (2-ethylhexanol) was returned to the flask until the reaction was complete. After distilling off the unreacted 2-ethylhexanol, the ethylhexyl cyanoacetate (bp 146° C./5 mm Hg) was isolated as a clear liquid. The average yield was 194 g (98.1% of theoretical) having a purity of 99.5% (GC assay).

EXAMPLE 2
Preparation of Isoamyl Cyanoacetate

Using the procedure of Example 1, cyanoacetate acid (85.5 g; 1.00 mol) and isoamyl alcohol (176 g; 2 mol) are reacted in the presence of sulfuric acid (0.49 g; 0.005 mol). Isoamyl cyanoacetate (bp 133/20 mm of Hg) is recovered as a clear liquid. The yield was 150 g (97% of theoretical) and its purity was >99% (GC assay).

EXAMPLE 3
Preparation of n-Propyl Cyanoacetate

Cyanoacetic acid (85.5 g; 1.0 mol), 1-propanol (120 g; 2.0 mol) and p-toluenesulfonic acid monohydrate (1.00 g; 0.005 mol) were introduced into a 500 ml flask. The mixture was slowly heated to a maximum of 105° C. while collecting distillates at 88–90° C. The pressure was reduced so that the flask was maintained at 105–110° C. and the distillates were collected continuously, and the propanol was returned to the flask. After distilling off the unreacted propanol, the n-propyl cyanoacetate (bp 100° C./23 mm Hg) was collected as a clear liquid. The yield was 122 g (96% of theoretical) and its purity was >99% (GC assay).

EXAMPLE 4
Preparation of Isopropyl Cyanoacetate

Cyanoacetic acid (85.5 g; 1.0 mol), isopropanol (80 g; 1.33 mol) and methanesulfonic acid (1.00 g; 0.01 mol) were introduced into a 500 ml flask. The mixture was slowly heated to a maximum of 105° C. while collecting distillates at 77–80° C. Additional isopropanol (220 g; 3.67 mol) was added to maintain the flask at 105–110° C. and the collection of distillates was continued at 77–80° C. After distilling off the unreacted isopropanol, the isopropyl cyanoacetate (bp 100° C./20 mm Hg) was collected as a clear liquid. The yield was 120 g (94.5% of theoretical and its purity was >99% (GC assay).

EXAMPLE 5
Preparation of Decyl Cyanoacetate

Cyanoacetic acid (85.5 g; 1.0 mol), decyl alcohol (206 g; 1.30 mol) and methanesulfonic acid (0.47 g; 0.005 mol) were introduced into a 500 ml flask under a nitrogen atmosphere. The mixture was warmed slowly to a maximum temperature of 130° C., while gradually reducing the pressure to about 10 mm of Hg. Water was continuously removed from the distillates (bp 60–65° C./50 mm of Hg) and the organic layer of decyl alcohol was returned to the flask until the reaction was complete. After distilling off the unreacted decyl alcohol, the decyl cyanoacetate (bp 143° C./1 mm of Hg) was isolated as a clear liquid. The yield was 219 g (97% of theoretical) with a purity of >99% (GC assay).

EXAMPLE 6
Preparation of Cyclohexyl Cyanoacetate:

Cyanoacetic acid (85.5 g; 1.0 mol), cyclohexanol (115 g; 1.15 mol) and methanesulfonic acid (0.47 g; 0.005 mol) were introduced into a 500 ml flask under a nitrogen atmosphere. The reaction vessel was equipped with a distillation column that is provided with means for recycling the alkanol distillate to the flask. The mixture was slowly warned to a maximum of 150° C. while collecting the distillates at 68–74° C. The pressure was gradually reduced to approximately 15 mm, so that the flask was maintained at 145–150° C. Water was removed continuously from the distillates (bp 68–8020 C./100 mm) and the organic layer (cyclohexanol) was returned to the flask until the reaction was complete. After distilling off the unreacted cyclohexanol, the cyclohexylcyanoacetate(bp 133/20 mm) was isolated as a clear liquid. The yield was 157 g (94% of theoretical) with a purity of >99%(GC assay).

As will be seen from the above examples, the invention provides a process suitable for the commercial production of the desired product that can be practiced without specialized reactors and results in high yields of product having excellent purity.

We claim:

1. An improved process for preparing a $C_{3-12}$ alkyl, substituted alkyl, alkenyl and cycloalkyl cyanoacetate product, which process comprises:

esterifying a $C_{3-12}$ alkyl, substituted alkyl, alkenyl or cycloalkyl alcohol by reaction with cyanoacetic acid in the presence of an acid catalyst in a reaction zone in accordance with reaction

$$CNCH_2COOH + R\text{—}OH \xrightarrow{(cat)} CNCH_2COOR + H_2O \qquad (I),$$

wherein R is a $C_{3-12}$ alkyl, substituted alkyl, alkenyl or cycloalkyl, and where the improvement comprises:
    (a) combining the cyanoacetate acid in crystalline form with the alcohol in a ratio from about 1:1.1 to about 1:4;
    (b) heating the reaction mixture of step (a);
    (c) removing the by-product water from the reaction mixture by distillation until the esterification reaction is substantially complete and substantially all of the water has been removed from the reaction zone;
    (d) removing the remaining alcohol from the reaction zone by distillation; and
    (e) recovering the cyanoacetate product.

2. A process according to claim 1 wherein the temperature in the reaction zone does not exceed the boiling point of the cyanoacetate product being formed.

3. A process according to claim 1 wherein the reaction is conducted at a temperature of about 60° C. to about 150° C.

4. A process according to claim 3 wherein the reaction is conducted at a temperature of about 70° C. to about 120° C.

5. A process according to claim 1 wherein the molar ratio of cyanoacetic acid to alcohol is about 1:1.1 to about 1:4.

6. A process according to claim 1 wherein the molar ratio of the cyanoacetic acid to the alcohol is about 1:1.3 to about 1:3.

7. A process according to claim 1 wherein the alcohol is selected from the group consisting of propanol, butanol, pentanol, isoamyl alcohol, hexanol, 2-ethyl hexanol, octanol and decyl alcohol.

8. A process according to claim 1 wherein the catalyst is selected from the group consisting of alkanesulfonic acids, alkylbenzenesulfonic acids, sulfuric acid and phosphoric acid.

9. A process according to claim 8 wherein the catalyst is methanesulfonic acid.

10. A process of claim 1 where at least one of the reactants is preheated to a predetermined reaction temperature before the reaction commences.

11. The process according to claim 1 in which distillate alcohol is carried over with distillate water in step (b) and the process further comprises:
   (f) separating the distillate alcohol carried over in the distillation of step (b) from the water; and
   (g) returning the separated dry distillate alcohol to the reaction zone.

12. A process according to claim 11 wherein the alcohol is propanol, isopropanol or butanol and an alcohol-water azeotrope is formed by the reaction in which the separation of the alcohol in step (a) comprises the further steps of contacting the alcohol-water mixture with a drying agent that removes the water from the mixture, and separating the alcohol from the drying agent.

13. The process according to claim 12 in which the drying agent is selected from the group consisting of phosphorus pentoxide, magnesium sulfate or sodium sulfate.

14. A process according to claim 11 wherein the alcohol is propanol, isopropanol or butanol and an alcohol-water azeotrope mixture is formed by the reaction in which the separation of the alcohol in step (f) comprises the further steps of (i) adding an organic solvent to the azeotropic mixture to form an extraction mixture; (ii) distilling the extraction mixture; and (iii) separating the alcohol as a distillate.

15. The process of claim 14 where the organic solvent is selected from the group consisting of pentane, hexane, cyclohexane, toluene and xylene.

16. A process according to claim 1 wherein the purity of the $C_3$–$C_{12}$ cyanoacetate is about 98% or greater.

17. A process according to claim 1 wherein the yield of the $C_3$–$C_{12}$ cyanoacetate is about 90% or greater.

* * * * *